United States Patent [19]

Yates

[11] 4,073,956
[45] Feb. 14, 1978

[54] FOAM TEXTURIZATION OF FUNGAL MYCELIAL FIBERS

[75] Inventor: Richard Alan Yates, Wilmington, Del.

[73] Assignee: E. I. Du Pont de Nemours and Company, Wilmington, Del.

[21] Appl. No.: 734,630

[22] Filed: Oct. 21, 1976

[51] Int. Cl.² .............................................. A23B 1/00
[52] U.S. Cl. .................................... 426/470; 426/574; 426/802; 426/564
[58] Field of Search ................. 426/60, 329, 470, 574, 426/802, 512, 474, 564; 264/202

[56] References Cited

U.S. PATENT DOCUMENTS

| | | | |
|---|---|---|---|
| 3,031,312 | 4/1962 | Morgan et al. | 426/470 |
| 3,889,010 | 6/1975 | Brouwer | 426/802 |
| 3,917,876 | 11/1975 | Harwood et al. | 426/802 X |
| 4,005,062 | 1/1977 | Schnell | 426/564 X |

FOREIGN PATENT DOCUMENTS 1,346,062   1974   United Kingdom .................. 426/60

Primary Examiner—R. B. Penland

[57] ABSTRACT

An aqueous suspension of a proteinaceous mass of fungal mycelial fibers is foamed with a gas such as air under shear conditions adequate to break the gas into bubbles small enough to be retained by the suspension but not so vigorous as to destroy the fungal mycelial fibers. The resulting slurry is filtered to remove most of the water while retaining the air. The resulting filter cake retains its foamed structure and can then be further processed if desired and air dried to produce a texturized meat-like product. In a preferred aspect of the invention the filter cake is sliced into strips, recompacted and dried to produce a product closely resembling meat in physical properties.

9 Claims, 3 Drawing Figures

FOAM TEXTURIZATION OF FUNGAL MYCELIAL FIBERS

BACKGROUND OF THE INVENTION

The present invention relates to edible protein products derived from fungal mycelial fibers obtained from a fermenter. When such a material, particularly if the ribonucleic acid coated thereof has been reduced, is mechanically worked and then directly air dried, it becomes very hard and tough-textured. Similarly, products made from the material by reduction of nucleic acid content and direct air drying also have an undesirable texture.

SUMMARY OF THE INVENTION

The present invention relates to a gas entrappment and drying process. The process involves foaming a fungal mycelial fibrous fermenter product, filtering the slurry, and oven drying the foamed filter cake. The process can produce a variety of products which can either resemble various meats in texture or can be similar to snack foods such as cheese puffs.

DETAILED DESCRIPTION

Figure 1:
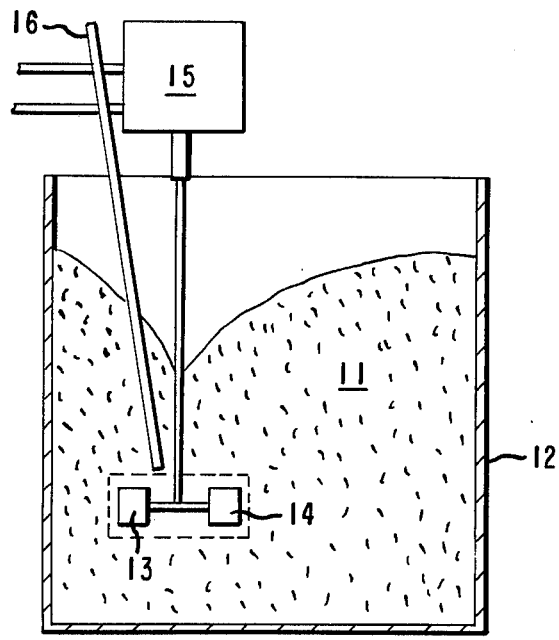
FIG. 1 is a schematic view of one form of the foaming apparatus used in the present invention.

The starting material for use in the present invention is generally prepared by fermentation of a nontoxic microfungus on an assimilable carbohydrate. The resultant product has a substantial protein content and is useful as food for both humans and animals. Various microfungi may be used to prepare the starting material. The preferred microfungus is *Fusarium graminearum* Schwabe deposited with the Commonwealth Mycological Institute and the American Type Culture Collection (A.T.C.C.) and assigned the numbers I.M.I. 145,425 and A.T.C.C. 20334. Suitable reisolates of this microfungus also deposited with the Commonwealth Mycological Institute (I.M.I.) and the American Type Culture Collection include I.M.I. 154,209, A.T.C.C. 20,329; I.M.I. 154,210, A.T.C.C. 20,333; I.M.I. 154,221, A.T.C.C. 20,330; I.M.I. 154,212, and I.M.I. 154,213, A.T.C.C. 20,322. Other suitable nontoxic microfungi include but are not limited to *Fusarium oxysporum* (I.M.I. 154,214, A.T.C.C. 20,328), *Fusarium solani* (I.M.I. 154,217, A.T.C.C. 20,327), and *Penicillium notatum chrysogenum* (I.M.I. 142,383; I.M.I. 142,384; I.M.I. 142,385; I.M.I. 142,386), with the numbers of strains thereof which have been deposited with the Commonwealth Mycological Institute or American Type Culture Collection given in parenthesis. A typical preparation of the starting material is as follows:

A continuous 8-liter fermenter is sterilized and continuously charged with a sterile medium consisting of

|  | g per 100 liters |
|---|---|
| $MgSO_4$ | 40.5 |
| $ZnSO_4 \cdot 7H_2O$ | 0.83 |
| $CuSO_4 \cdot 5H_2O$ | 0.167 |
| $MnSO_4 \cdot 1H_2O$ | 0.63 |

-continued

|  | g per 100 liters |
|---|---|
| $FeSO_4 \cdot 7H_2O$ | 0.83 |
| $K_2SO_4$ | 10.0 |
| $(NH_4)_2SO_4$ | 144.0 |
| $NaMoO_4 \, 2H_2O$ | 0.083 |
| $CoCl_2 \cdot 6H_2O$ | 0.17 |
| NaCl | 10.0 |
| $CaCl_2$ | 8.0 |
| $KH_2PO_4$ | 379.0 |
| Biotin | 0.0006 |
| Dextrose . $H_2O$ | 8,000.0 |
| Ammonium citrate | 4.0 |
| Boric acid | 0.05 |
| Water | to 100 liters |

The rate of charging the sterile medium is 1.18 liters per hour. The medium in the fermenter is inoculated with a spore suspension of the organism or organisms indicated above. The fermenter is stirred with a 6-bladed disc turbine operated at 850 rpm. Air is flowed through the fermenter at a rate of 3.6 liters per minute. Additional oxygen flow is 2.0 liters per minute. The fermenter temperature is 29.2° C, and the pH is 4.8. Ammonia is added to control the pH and provide additional mycelial nutrient. The fermenter productivity is 5.4 grams per liter hour. The product fungal mycellium is continuously drawn off the fermenter, and collected in a product receiver which is held at 8° C. After steady operation is achieved the pooled product for 10 hours operation is then harvested. Sufficient filter cake to give the concentration indicated under cell weight percent in slurry in Tables 2 and 3 is suspended in 8.0 liters of filtrate which has been preheated to 72° C and which is adjusted with NaOH to pH 6. Addition of the cake decreases the temperature, and the slurry is maintained at 64° C for twenty minutes. This treatment serves to reduce the nucleic acid content of the filter cake so that higher levels of ingestion of the material by humans is possible. This step also serves to rovide the slurry with an agent which has not been positively identified, which serves as a foam stabilizer. If the slurry is filtered and washed with fresh water at this point the foam stabilization will be reduced. The slurry is aerated with stirring adequate to generate small bubbles, but insufficient to break hyphal fibers. The slurry with entrapped air is then partially dewatered to give 20 to 30% solids. At this point the material comprises an entangled mass of limp flexible mycelial filaments with entrapped flattened air bubbles. It is an open network with fibers in random orientation except in regions where they have been drawn into some order by mechanical work. Since the fibers are flexible, interfilament contacts are frequent and involve relatively large areas of surface contact.

Referring now to FIG. 1 the mass of wet fungal mycelial RNA reduced fibers 11 is placed in container 12. Flat bladed turbine 13 mounted in foraminous housing 14 is driven by motor 15. In the Examples the container used is a 4-liter cylindrical container containing 3 liters of slurry, the agitator is a Silverson mixer, about 50 mm in diameter, has 6 blades, is operated at about 600 rpm for 1 minute, and the holes in the foraminous housing are about 3 mm in diameter. Tube 16 is connected to means not shown adapted to feed a predetermined amount of gas such as air to the turbine which enables the gas entrappment in the fungal mycelial fibrous matrix. The amount of gas added generally will be enough to provide a foam density of rom 2 to 8 milliliters of gas per gram of solids (solids as used herein are calculated as dry hyphal weight). With foam densities below about 2 ml of gas per gram of solids the product after air drying and rehydration is tough and similar to cardboard in texture. Foam densities above about 8 ml of gas per gram of solids result in products after drying and rehydration which have poor strength and integrity. The preferred density for producing meat-like products is from 3 to 4 ml of gas per gram of solids. For producing snack foods similar to chesse puffs foam densities of from 5 to 6 ml of ga per gram of solids are preferred. The speed at which the turbine is driven is dependent on the size and design of the turbine. The speed should no be so high that significant breakage of the fungal hyphae occurs but must be fast enough to shear the gas into fine bubbles. Coarse bubbles tend to escape from the foam and further result in a product having a somewhat coarser structure than is preferred. Generally, 90% of the bubbles should be from below 3 mm in diameter. Generally, the foam is stable from 30 minutes to one hour after which time the foamed hyphal mass tends to rise appreciably leaving clear liquid at the bottom of the vessel. If this occurs restirring may be done if desired but is not necessary. Foam stability is largely dependent on the average hyphal length of the product. Preferably at least 25% of the hyphae will be longer than 0.5 mm. With less than 10% of hyphae longer than 0.5 mm foam stability is impracticably short and the product is poor.

It is not important whether the short hyphae represent an environmental form of the long fibers or a genetic variant so long as the proportion of long hyphae is adequate.

The temperature at which the foaming takes place is not critical and 0° C to 100° C can be used. From 15° C to 70° C is the preferred range. Binders such as gluten can be added to the slurry prior to foaming but are not necessary. Generally the foam will contain from 1 to 6 weight percent solids (dry hyphae basis).

The foam is then filtered to reduce its moisture content. The technique used to filter the foam is not critical. If average hyphal length is long, generally vacuum filtration is used. Generally, the thickness of the cake being filtered will be from 3 to 20 mm (optimum 6–12 mm). There should be from 0.1 to 0.9 atm pressure drop across the filter cake. Below about 0.1 atm pressure drop the time needed becomes inordinately long. Above about 0.9 atm pressure drop there is a tendency to collapse the foam structure. The filtration step serves to reduce the moisture content of the filter cake to from 18 to 34 weight percent, while retaining almost all of the hyphae and air.

In the Examples the filtration is done on a Buckner funnel on filter paper using a ½ atm pressure drop; however, screens can be used. A pressure head on the upstream side of the filter cake can be used so that when the pressure is rapidly released after filtration some reexpansion can be achieved.

Figure 2:
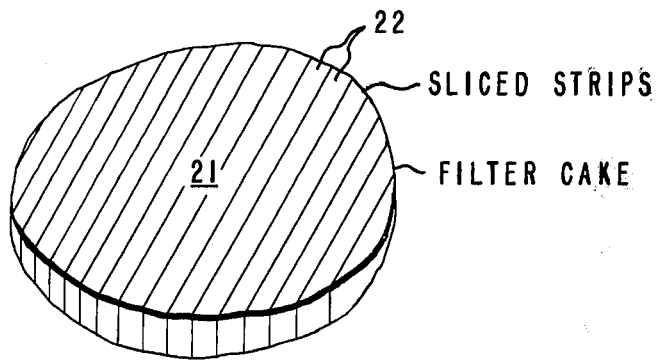
FIG. 2 is a view of the sliced foamed filter cake of the present invention.
Figure 3:
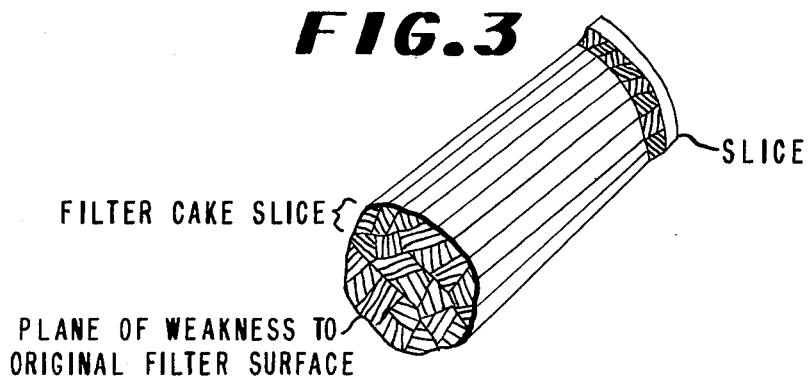
FIG. 3 is one example of filter cake processed to give meat-like texture.

In a preferred aspect of the invention as shown in FIG. 2 the filter cake 21 is sliced in a generally perpendicular direction into strips 22. The strips generally are from 6 to 12 mm in thickness and as wide as the filer cake. The strips are then reassembled as shown in FIG. 3 so that the axis of adjoining strips are at 45° to 90° to each other with respect to their original orientation and the mass compacted and lengthened as by rolling or squeezing, after which slices can be made. The resulting product has planes or weakness more nearly like that of meat than is the case when the untreated filter cake is simply dried. Alternatively, the filter cake can be rolled up on itself, compacted, and sliced or can be extruded through a mesh, recompacted, and sliced.

The filter cake is now dried. Generally, the drying is done at 50° C to 90° C is an air oven. The drying serves to reduce the moisture content of the product to below 5 weight percent with about 3 weight percent moisture being preferred. The drying serves to improve the shelf life of the product. The dried product can be rehydrated to absorb from 1 to 5 and preferably 1.5 to 3.0 times its weight of water. After squeezing and blotting the water content decreases to a maximum of abou twice the solids content. In contrast an unfoamed filter cake when dried in an air oven will only take up from 0.2 to 0.5 times the solid's weight of water. Alternately the compacted, foamed log of material can be partly dried before slicing to give an improved surface appearance, then the slices dried completely, or the product can be dried as a log and then sliced after rehydration.

EXAMPLE 1

A mycelial slurry of *Fusarium graminearum* Schwabe I.M.I. 145,425, grown and treated as described above to reduce the nucleic acid content, and containing 31.4 g dry weight per liter, was gassed with $N_2$ at about 4 ml $N_2$ per gram dry weight, filtered, washed with 0.6 bed volume distilled water, sliced, and dried in a 60° hot air oven for 16 hours. Another aliquot of the same slurry was similarly treated, except that it was not gassed. Pieces of the dried filter cakes were rehydrated by either heating 10 minutes in 90° C water or by autoclaving at 18 psi for 5 minutes in water, then blotted, weighed, squeeze blotted between 3 layers of paper towels and reweighed. Alpha-amino nitrogen 72 mg/g; RNA 26 mg/g.

TABLE 1

| Example | Sample | Rehydration | blotted | Ratio of hydrated/dry squeeze blotted | Comments |
| --- | --- | --- | --- | --- | --- |
| 1-1 | Control | hot water | .60 | .56 | woody |
| 1-2 | | autoclaved | .94 | .84 | woody |
| 1-3 | Aerated | hot water | 1.56 | 1.22 | resilient |
| 1-4 | | autoclaved | 2.90 | 1.65 | resilient |

EXAMPLE 2

A mycelial slurry of *Fusarium graminearum* Schwabe I.M.I. 145 425 was grown in a 1300 l continuous fermenter, and treated as described above to reduce the nucleic acid content. The fermenter medium differed in using process water, containing 3.6 fold as much calcium, and using potato starch hydrolysate in place of pure glucose as substrate in the medium reported above. Some of the samples were filtered and resuspended in water before foaming, other samples had gluten added prior to foaming, some samples were filtered without air foaming as controls. Sample slurries were tested at varied cell concentrations and varied ratios of air to cell mass. Product filter cakes were sliced and dried in a hot air oven; weighed pieces were rehydrated in boiling water, squeeze blotted, and reweighed as described above to determine the ratio of water to dry weight held by the rehydrated products. Data is shown in Table 2.

TABLE 2

| Sample Code | RNA-Reduction Solubles Present | Gluten as Percent of Dry Weight | Ml Air in Slurry Per Dry Weight | Cell Weight Percent in Slurry | Oven Air Dry °C | Hours | Rehydration Water/Dry Weight 10'Boil | 30'Boil | Comments on Rehydrated Samples |
|---|---|---|---|---|---|---|---|---|---|
| 2-1 | Yes | 10 | None | 6 | 60 | 15 | 0.3 | 0.5 | very tough & hard |
| 2-2 | Yes | 10 | 0.6 | 6 | 60 | 15 | | 0.6 | very tough; hard |
| 2-3 | Yes | 10 | 1.2 | 6 | 60 | 15 | | 0.8 | tough; slight resilience |
| 2-4 | Yes | 11 | 2.4 | 6 | 60 | 15 | | 1.5 | resilient-firm |
| 2-5 | Yes | 11 | 4.8 | 6 | 60 | 15 | | 2.3 | resilient-weak |
| 2-6 | Yes | 5 | ca 4 | 6 | 50 | 15 | 1.0 | 1.4 | resilient-firm |
| 2-7 | Yes | None | 2.5 | 6 | 60 | 15 | | 1.0 | semi-resilient |
| 2-8 | Yes | None | ca 4 | 5 | 50 | 15 | 1.2 | (est 1.5) | resilient-firm |
| 2-9 | No | 5 | ca 4 | 9 | 50 or 70 | 15 | 0.5 | (est 0.8) | tough; hard; slight resilience |

EXAMPLE 3

A mycelial slurry of *Fusarium graminearum* Schwabe I.M.I. 145,425 was grown as described above for Example 1, except stir rate was 500 rpm, air flow 11 l/minute, no oxygen flow, growth rate 0.14 hr$^{-1}$, productivity 3 g/l/hr, pH 5.3. Product was treated to reduce nucleic acid as described above, then aliquots of slurry were adjusted to different cell mass levels, aerated with different ratios of air to cell mass during agitation, filtered, washed with 1 bed volume of water, and sliced as described in Example 1. Part of the filter cake was dried directly as slices for 16 hours in a 60° C hot air oven. Part of the filter cake slices were aligned with random rotation directions to randomize the planes of weakness established during filtration, recompacted into a "log" with about two-fold radial compression and corresponding linear extension, leaving a "log" diameter of about 3 to 4 inches. Part of the "log" was sliced at an angle, giving slices ¼ to ½ inch thick, and the remainder left as a large chunk. Slices and chunks were also dried in a hot air oven as described above. Weighed samples of strip, slice, and chunk were rehydrated by immersion in water during 10 minute autoclaving at 18 psi steam pressure, and the rehydrated products squeeze blotted between layers of paper towels. The samples were reweighed and the ratio of water to dry weight calculated, and the products assessed for resilience. Data is shown in Table 3.

TABLE 3

| Sample Code | Cell Weight Percent in Slurry | Ml. Air in Slurry Per g Dry Weight | Rehydration Water/Dry Weight Strip | Slice | Chunk | Comments |
|---|---|---|---|---|---|---|
| 3-1 | 24 | 4.2 | 2.2 | 2.1 | 1.8 | resilient-firm |
| 3-2 | 16 | 4.1 | 1.9 | 2.0 | 1.9 | " |
| 3-3 | 8 | 4.0 | 2.6 | 2.1 | 2.1 | resilient-slightly soft |
| 3-4 | 16 | 8.3 | 2.8 | 2.3 | 2.5 | resilient-soft |
| 3-5 | 16 | 16.8 | 2.4 | 2.1 | 2.0 | very soft-collapsed during squeeze blotting |
| 3-6 | 16 | 0 | 1.3 | 1.3 | 1.1 | tough, dense (leathery & woody) |

EXAMPLE 4

Two mycelial slurries of *Fusarium graminearum* Schwabe I.M.I. 145,425 were grown and nucleic acid reduced as described in Example 2, except that the average hyphal lengths were quite different. One culture ("long") had half of the cell mass in fibers above 0.40 mm long (35% of the mass in hyphae over 0.5 mm long, 10% over 1 mm) while the other culture ("short") had half of the mass in fibers above or below 0.2 mm (<2% above 0.5 mm). When 200 ml of RNA-reduced slurry, 23 g/l cell mass, were passed through a 0.25 mm screen of 910 mm$^2$ area at a pressure differential of 4 psi, the "long" culture required 41 seconds while the "short" culture required 8 seconds (water required 4.5 seconds).

The "short" and "long" RNA-reduced hyphal slurries at ca 23 g/l were aerated at ca 4 ml air/g, filtered, sliced, air dried, weighed, rehydrated by 30 minute boiling, drained, squeeze-blotted and reweighed. The "short" slurry had to be filtered quickly at the end of air blending to prevent air bubbles rising from the slurry; air entrappment in the "long" slurry was stable.

TABLE 4

| Sample Code | Sample | Rehydration Water/Dry Weight | Comments on Rehydrated Product |
|---|---|---|---|
| 4-1 | "long" | 1.6 | resilient; did not mash or crumble |
| 4-2 | "short" | 1.6 | poorly resilient; mashed and crumbled easily |

What is claimed is:

1. A process comprising foaming an aqueous suspension of a fibrous proteinaceous hyphal fungal mass which contains from 10 to 35 weight percent solids, wherein the ribonucleic acid content of the fungal mass has been reduced to below 4 weight percent, and wherein at least 10% of the hyphae forming the fibrous proteinaceous hyphal mass are longer than about 0.5 mm to a density of from 2 to 8 milliliters of gas per gram of dry weight fungal mass to form a foamed slurry, filtering the foamed slurry to reduce the moisture content thereof to form a filtered foam, and drying the filtered foam to reduce the moisture content thereof to below 5 weight percent.

2. The process of claim 1 wherein the foaming is carried out by adding air to a stirred vessel containing the aqueous suspension of the fibrous proteinaceous fungal mass.

3. The process of claim 2 wherein the fungal mass is *Fusarium graminearum* Schwabe.

4. The process of claim 3 wherein the filtered foam contains from 18 to 32 weight percent solids.

5. The process of claim 4 wherein the foamed slurry contains from 1.0 to 6 weight percent solids.

6. The process of claim 5 wherein the foamed slurry contains from about 3 to about 4 milliliters gas per gram hyphal dry weight.

7. The process of claim 6 wherein the filtered foam is sliced into strips from 6 to 12 mm in width which are reassembled and compacted together prior to the drying step.

8. The process of claim 7 wherein the drying step is done at from 50° to 100° C.

9. The process of claim 8 wherein the drying step reduces the moisture content to about 3 percent moisture.

* * * * *

UNITED STATES PATENT OFFICE
CERTIFICATE OF CORRECTION

PATENT NO. : 4,073,956

DATED : February 14, 1978

INVENTOR(S) : Richard Alan Yates

It is certified that error appears in the above-identified patent and that said Letters Patent are hereby corrected as shown below:

Column 1, line 22, "product" should read --produce--.

Column 1, line 49, "154,221" should read --154,211--.

Column 2, line 38, "rovide" should read --provide--.

Column 2, line 67, "rom" should read --from--.

Column 3, line 9, "chesse" should read --cheese--.

Column 3, line 10, "ga" should read --gas--.

Column 3, line 13, "no" should read --not--.

Column 4, line 13, "abou" should read --about--.

Column 4, line 42, Table 1, "Ratio of hydrated/dry" should read --Ratio of hydrated/dry weights--.

Column 5, line 4, Table 2, "Ml Air in Slurry Per Dry Weight" should read --Ml Air in Slurry Per g Dry Weight--.

Column 5, line 26, "ofthe" should read --of the--.

Signed and Sealed this

Twentieth Day of June 1978

[SEAL]

Attest:

RUTH C. MASON
Attesting Officer

DONALD W. BANNER
Commissioner of Patents and Trademarks